United States Patent
Soukup

(10) Patent No.: US 7,115,643 B2
(45) Date of Patent: Oct. 3, 2006

(54) INTERMEDIATE HALOPHENYL DERIVATIVES AND THEIR USE IN A PROCESS FOR PREPARING AZOLE DERIVATIVES

(75) Inventor: Milan Soukup, Bottmingen (CH)

(73) Assignee: Basilea Pharmaceutica AG, Basel (CH)

( * ) Notice: Subject to any disclaimer, the term of this patent is extended or adjusted under 35 U.S.C. 154(b) by 148 days.

(21) Appl. No.: 10/481,654

(22) PCT Filed: Jun. 17, 2002

(86) PCT No.: PCT/EP02/06644

§ 371 (c)(1),
(2), (4) Date: Dec. 22, 2003

(87) PCT Pub. No.: WO03/002498

PCT Pub. Date: Jan. 9, 2003

(65) Prior Publication Data

US 2004/0176432 A1    Sep. 9, 2004

(30) Foreign Application Priority Data

Jun. 26, 2001 (EP) .................... 01115355

(51) Int. Cl.
*A61K 31/41* (2006.01)
*C07D 249/08* (2006.01)
(52) U.S. Cl. ..................... 514/383; 548/267.8
(58) Field of Classification Search ............... 514/383; 548/267.8
See application file for complete search history.

(56) References Cited

U.S. PATENT DOCUMENTS 5,072,037 A    12/1991    Weber et al.
5,366,989 A *  11/1994    Imaizumi et al. ........... 514/383
5,395,942 A    3/1995     Worthington

FOREIGN PATENT DOCUMENTS

EP    0436860 A1    7/1991
EP    0617031 A1    9/1994
EP    0667346 A2    8/1995
WO    WO 92/17474   10/1992

OTHER PUBLICATIONS

An et al., Synthesis of Chiral Alkynes Having 2H or Halogen at the Secondary or Tertiary Propargylic Stereogenic Center by Hydrolysis and Halogenolysis of Optically Active Allenyltitaniums Having Axial Chirality, Tetrahedron Letters, 39(25):4555-8 (Jun. 18, 1998).
Tanaka, et al., Triazole Antifungals. V. Synthesis and Antifungal Activities of Some Amides Related to Acylamino-2-aryl-1-triazolyl-2-butanol, Chemical and Pharmaceutical Bulletin, 40(3):661-5 (1992).

* cited by examiner

Primary Examiner—Joseph K. McKane
Assistant Examiner—Susannah L. Chung
(74) Attorney, Agent, or Firm—Gibbons, Del Deo, Dolan, Griffinger & Vecchione

(57) ABSTRACT

Novel halophenyl derivatives of the general formula (I), wherein $R^1$ is halogen, a leaving group or 1H-1,2,4-triazol-1-yl and $R^2$ is ethynyl or carboxy, $X^1$ is halogen and $X^2$ and $X^3$ are each independently hydrogen or halogen, and their manufacture are described. They are intermediates for manufacturing azole derivatives of the general formula (V) which are valuable medicaments useful for treating systemic mycoses.

28 Claims, No Drawings

INTERMEDIATE HALOPHENYL DERIVATIVES AND THEIR USE IN A PROCESS FOR PREPARING AZOLE DERIVATIVES

Azole derivatives of the general formula

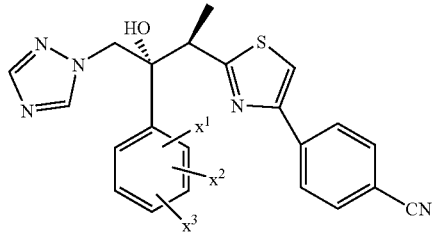

V wherein $X^1$ is halogen and $X^2$ and $X^3$ are each independently hydrogen or halogen, are valuable medicaments useful for treating systemic mycoses and possess a broad antifungal spectrum. However, heretofore they have been available only by multistep linear synthesis with low overall yield and low diastereoselectivity with respect to the (1R,2R)-propyl moiety of the molecule (EP 0667 346 A2, South African Patent 99/1763, WO 01/32652).

It has now surprisingly been found that the azole derivatives aforesaid can be manufactured in a much simplified manner using considerably less process steps and with considerably improved yield and diastereoselectivity. The process which offers these adventages can be depicted by the following Scheme 1:

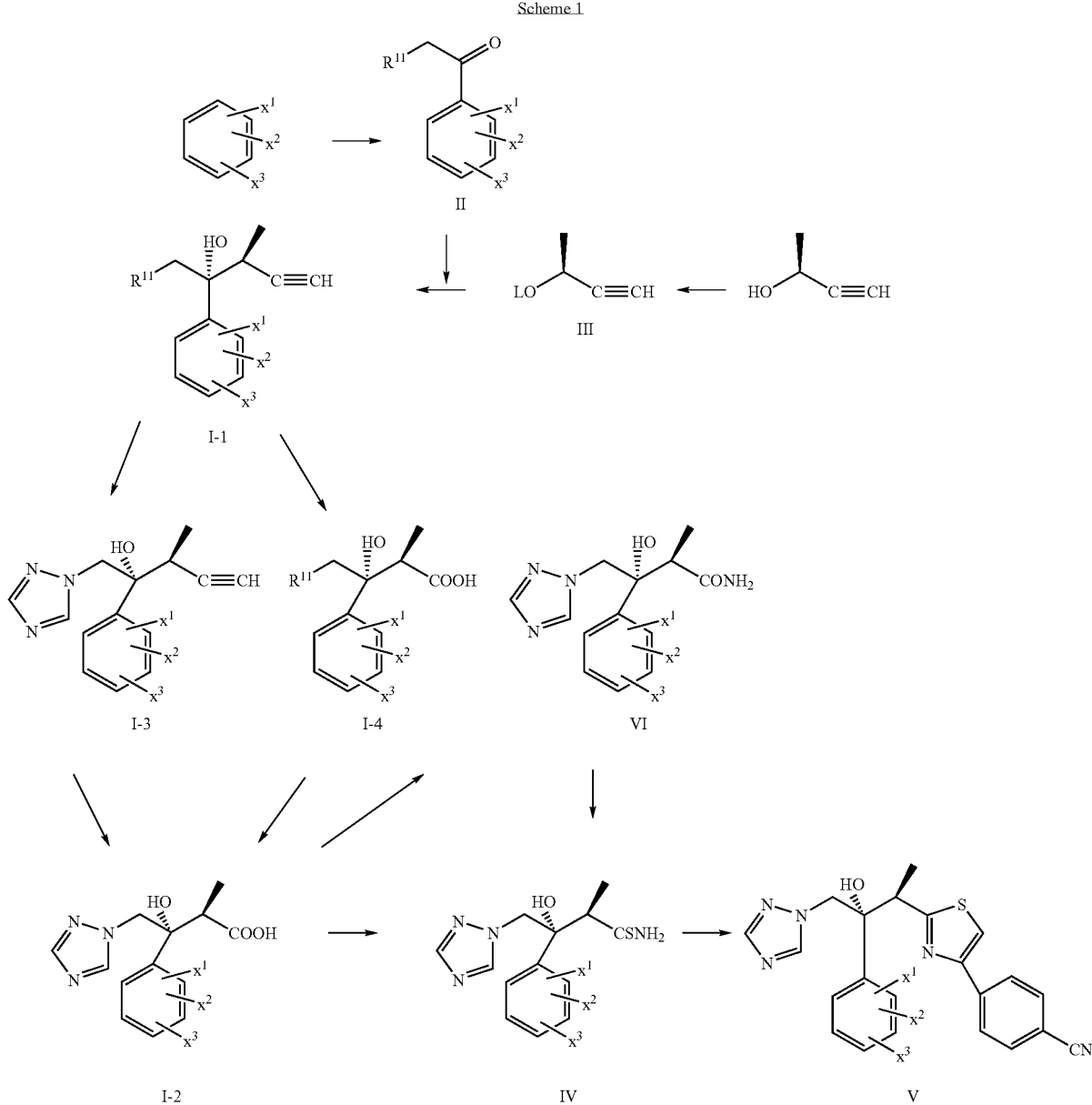

wherein the symbols have the significance given below.

Thus, in a first embodiment, the invention concerns novel intermediates of the general formula

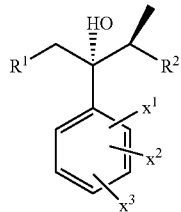

I wherein R¹ is halogen, a leaving group or 1H-1,2,4-triazol-1-yl and R² is ethynyl or carboxy, X¹ is halogen and X² and X³ are each independently hydrogen or halogen.

In the above scheme 1, formulas I-1, I-2, I-3 and I-4 are comprised by the above formula I.

In a second embodiment, the invention concerns the diastereoselective synthesis of halophenyl derivatives of the general formula

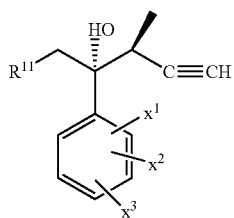

I-1 wherein $R^{11}$ is halogen or a leaving group, X¹ is halogen and X² and X³ are each independently hydrogen or halogen, which is characterized in that it comprises reacting a halophenyl derivative of the general formula

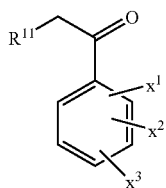

II wherein $R^{11}$, X¹, X² and X³ are as above, with an alkyne of the general formula

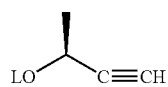

III wherein L is halogen or a leaving group, in the presence of a palladium catalyst and an organometallic reagent in an apolar organic solvent.

In this process $R^{11}$ and L signify halogen, preferably chloro or bromo, particularly chloro, or a leaving group such as lower alkylsulphonyl, phenylsulfonyl or lower alkylsulfonyl, e.g. methylsulfonyl (mesyl), phenylsulfonyl or p-tolylsulfonyl (tosyl). $R^{11}$ is preferably chloro, L is preferably mesyl.

The reaction between compounds II and III is carried out in the presence of a palladium catalyst in an apolar organic solvent. This catalyst is preferably a Pd(0)organic complex, a Pd(II)salt or an organic complex thereof. Examples of these catalysts are tetraphosphinyl palladium, palladium dichloride, palladium diacetate or an organic complex thereof, e.g. the diacetonitrile complex. Preferably the reaction is carried out in the presence of a phosphine ligand such as triphenylphosphine. The reaction proceeds in the presence of an organometalic reagent, preferably an excess of a di-(lower alkyl)-metal reagent in which the metal is selected from Li, Mg, Zn, Sn and Al. The preferred metal is zinc; the preferred reagent is diethylzinc. The preferred apolar organic solvent for the reaction is n-hexane, toluene and tetrahydrofuran. The temperature of the reaction preferably lies in the range of −40° C. to +40° C., particularly +25° C. to +30° C. The reaction product is subsequently worked up in usual manner and extracted with an organic solvent such as ethyl acetate.

In the resulting compound I-1 $R^{11}$ is replaced by the 1H-1,2,4-triazole group and the ethynyl group is oxidized to carboxy; while these reaction steps can be carried out in any order, it is preferred to introduce the 1H-1,2,4-triazole group first, leading to compounds I-3, followed by oxidation to yield compounds I-2.

The reaction of compounds I-1 and I-4 with 1H-1,2,4-triazole is carried out in a polar or apolar organic solvent, e.g. dimethyl sulfoxide, dimethyl formamide, tetrahydrofuran or a lower alkanol such as methanol, ethanol or isopropanol in the presence of a base. As base preferably an alkali metal hydroxide or hydride is used, most preferably sodium hydroxide. The temperature lies advantageously in the range of 40–80° C. The reaction products of formulas I-3 and I-2 are preferably recovered as water-soluble N-quaternary salts by the addition of acid such as hydrochloric acid or oxalic acid.

Compounds I-1 and I-3 are oxidized to introduce carboxy in lieu of ethynyl. The oxidation is carried out in a solvent, e.g. water, acetic acid or ethyl acetate and is preferably effected by treatment with an alkali metal periodate (e.g. sodium(meta)periodate) or hypochlorite in the presence of a catalyst such as ruthenium dioxide. Another oxidation agent is alkali metal permanganate. The oxidation is preferably carried out at a temperature of about 40–70° C. and in the presence of a phase transfer reagent for oxidations, such as trialkyl($C_8/C_{10}$)methylammonium chloride (ADOGEN® 464).

The carboxylic acids of formulas I-2 are converted to the thioamides IV e.g. by reaction with a dithiophosphoric acid 0,0-di-(lower-alkyl)ester and either of ammonia or hexamethyldisilazane in an organic solvent, e.g. with 0,0-diethyldithiophosphate and hexamethyldisilazane in toluene. Preferred temperature range is 60–80° C. An alternative thioamidation process is conversion of the carboxylic acid I-2 to the acid amide VI with carbonyldiimidazole to yield the corresponding β-lactone, subsequently with aqueous ammonia and subsequent reaction of the acid amide VI obtained with 2,4-bis-(4-methoxyphenyl)-1,3,2,4,dithiadiphosphetan-2,4-dithion (Lawesson reagent) in an inert organic solvent, e.g. tetrahydrofuran, at a temperature of room temperature to about 80° C.

Another possibily is to dehydrate the acid amide VI into the nitrile with phosphoroxychloride at about 30 to 50° C. and subsequenty transformation of the nitrile into thioamide by standard methods such as HSPS(OEt)$_2$ in water or aqueous (NH$_4$)$_2$S at about 70° C.

Compounds IV are finally reacted with 2-bromo-4'-cyanoacetophenone to yield the desired end products of formula V, preferably in an inert organic solvent such as acetonitrile, ethanol or methanol at a temperature between room temperature and about 80° C. This reaction is described also in EP 0667 346 A2, South African Patent 99/1763 and WO 01/32652.

The significance of $X^1$, $X^2$ and $X^3$ in the above formulas is dictated by the therapeutic activity of the compounds V as antifungal agents; preferably $X^1$ is 2-fluoro, $X^2$ is hydrogen and $X^3$ is 4-fluoro or 5-fluoro.

The following examples illustrate the invention in more detail.

EXAMPLE 1

1.062 g (4.092 mmol) of palladium(II)-dichloride diacetonitrile were dissolved in 380 ml of tetrahydrofuran. 2.710 g (10.23 mmol) of triphenylphosphine were added at room temperature. The reaction mixture turned yellow and, after about 5 minutes, turbid. Stirring was continued at room temperature for 10 minutes whereafter 27.29 g (184.1 mmol) of (R)-methanesulfonic acid 1-methyl-prop-2-ynylester and 19.50 g (102.3 mmol) of 2-chloro-1-(2,5-difluoro-phenyl)-ethanone were added. About 30 ml of a solution of 279.0 ml (306.9 mmol) of diethylzinc solution in toluene (1.1 M; 100%) were added dropwise so as to enable the temperature to rise to 36° C. The rest of said diethylzinc solution was added dropwise within 13 minutes at 37–38° C., whereafter the temperature was maintained below 39° C. by cooling. Stirring was continued for 40 minutes (temperature 26° C.). The reaction mixture was poured onto a mixture of 80.00 ml (614.4 mmol) of 25% aqueous hydrochloric acid and 800 ml of deionized water (with ice).

The reaction mixture was extracted three times with each 400 ml of ethyl acetate, the organic phases washed twice with each 250 ml of 5% aqueous sodium chloride solution, combined, dried over sodium sulfate, evaporated, again dissolved in about 100 ml of ethyl acetate, dried over sodium sulfate and evaporated to dryness. 31.45 g of (2R,3S)-1-chloro-2-(2,5-difluoro-phenyl)-3-methyl-pent-4-yne-2-ol were obtained as a yellow oil containing 86.5% of the stated diastereomer. Purity 67.4%. Yield 84.7%.

NMR (CDCl$_3$): 1.20 (d,3H9, 2.2 (s,1H), 2.70 (bd,1H), 3.20 (q,1H), 4.20 (m,2H), 6.9–7.4 (m,3H).

The 2-chloro-1-(2,5-difluoro-phenyl)-ethanone used as starting material was prepared as follows:

100.0 g (876.5 mmol) of 1,4-difluorobenzene and 90.83 ml (1139 mmol) of chloroacetyl chloride were cooled to 10° C. Within 5 minutes at 10–17° C. 153.5 g (1139 mmol) of aluminium chloride (99%) were added and the mixture warmed to room temperature. The mixture was heated for 30 minutes to 60° C. and the heating continued at this temperature for another 70 minutes. The reaction mixture was cooled to room temperature and poured onto a mixture of 0.8 l of ice and 400 ml at concentrated aqueous hydrochloric acid, extracted twice with each 500 ml of ethyl acetate, and the organic phases were washed once with 200 ml of water, three times with 400 ml of half-saturated aqueous sodium bicarbonate solution, dried over sodium sulfate, dissolved for 1 hour at 80° C. in 400 ml of n-hexane and, after the addition of 4 g of active carbon, filtered hot, stirred at room temperature and cooled to 0° C.; the crystals formed were dried at room temperature under reduced pressure to give 104 g (69%) of 2-chloro-1-(2,5-difluoro-phenyl)-ethanone.

NMR (CDCl$_3$): 4.72 (d,2H), 7.10–7.30 (m,2H), 7.60–7.70 (m,1H).

The (R)-methanesulfonic acid 1-methyl-prop-2-ynyl ester used above was prepared as follows:

25.30 g (353.7 mmol) of (R)-(+)-butyn-2-ol in 190 ml of methylene chloride were cooled to −78° C. and 99.09 ml (707.4 mmol) of triethylamine and 41.23 ml (530.5 mmol) of methanesulfochloride added carefully within 1 hour at −78° C. with stirring. The reaction mixture was poured onto 200 ml of half-saturated aqueous sodium bicarbonate, extracted twice with each 100 ml of methylene chloride, the organic phase washed with water, dried over sodium sulfate, filtered and evaporated. 76.2 g of raw product was obtained which was filtered on 50 g of silica gel with 2 l of methylene chloride and the 2 first fractions (2×500 ml) collected. After evaporation of the solvent 52.4 g (100%) of (R)-methanesulfonic acid 1-methyl-prop-2-ynyl ester were obtained as a slightly yellow liquid.

NMR (CDCl$_3$): 1.66 (d,3H), 2.71 (s,1H), 3.13 (s,3H), 5.29 (q,1H).

EXAMPLE 2

887.3 mg (3.423 mmol) of palladium(II)-dichloride-diacetonitrile were dissolved in 325.0 ml of tetrahydrofuran. 2.243 g (8.530 mmol) of triphenylphosphine were added. The reaction mixture turned yellow and, after 6 minutes, turbid. The reaction mixture was stirred for 10 minutes at room temperature, whereafter 22.81 g (153.9 mmol) of (R)-methanesulfonic acid 1-methyl-prop-2-ynylester and 16.30 g (85.52 mmol) of 2-chloro-1-(2,5-difluoro-phenyl)-ethanone were added together with about 25 ml of totally 233.3 ml (256.6 mmol) of diethylzinc solution in toluene (1.1 M) dropwise. The temperature was permitted to rise to 36° C. The remaining diethylzinc solution was added dropwose within 12 minutes at 37–38° C., whereafter the temperature was prevented from rising over 39° C. After 40 minutes (temperature about 27° C.) the reaction mixture was poured onto 350 ml of ice-cold half-saturated aqueous sodium chloride solution, 500 ml of ethylacetate were added, the mixture was stirred for 5 minutes at room temperature, and 70 ml of 25% aqueous hydrochloric acid were added (everything in solution). The aqueous phase was washed once with 250 ml of ethyl acetate and the organic phases once with 150 ml of quarter-saturated aqueous sodium bicarbonate solution and once with 50 ml of 0.1N aqueous hydrochloric acid. The organic phases were combined, dried over sodium sulfate and evaporated to dryness. 24.85 g of (2R,3S)-1-chloro-2-(2,5-difluoro-phenyl)-3-methyl-pent-4-yne-2-ol were obtained, which were 70.5% pure and contained 86% of the stated diastereomer. Yield 83.1%.

The NMR spectrum was identical to that described in Example 1.

EXAMPLE 3

16.33 mg (0.0630 mmol) of palladium(II)-dichloride-diacetonitrile were dissolved in 6.00 ml of tetrahydrofuran. 41.29 ml (0.157 mmol) of triphenylphoshine were added. The reaction mixture turned yellow and was stirred for 10 minutes at room temperature. 419.8 mg (2.833 mmol) of (R)-methanesulfonic acid 1-methyl-prop-2-ynylester and 300.0 mg (1.574 mmol) of 2-chloro-1-(2,4-difluorophenyl)-ethanone were added, also 4.293 ml (4.722 mmol) of diethylzinc solution in toluene (1.1 M) within 5 min. at 25–35° C., the latter dropwise with intermittent cooling of the reaction mixture. Stirring was continued for 45 min. at room temperature. The reaction mixture was added to 10 ml of ice-cold water and 5 ml of 25% aqueous hydrochloric acid, extracted twice with each 25 ml of ethyl acetate, the organic phases washed once with 15 ml of water, combined, dried over sodium sulfate and evaporated to dryness. 444 mg of (2R,3S)-1-chloro-2-(2,4-difluoro-phenyl)-3-methyl-pent-4-yne-2-ol were obtained as a yellow oil with purity 78.6%, which contained 77% of the stated diastereomer. Yield 90.6%.

NMR (CDCl$_3$): 1.22 (d,3H), 2.2 (6d,1H), 2.7 (vbs,1H), 3.20 (q,1H), 4.20 (dxd,2H), 6.70–6.90 (1m,2H), 7.20–7.70 (m,1H).

EXAMPLE 4

163.3 mg (0.630 mmol) of palladium(II)-dichloride-diacetonitrile were dissolved in 60.00 ml of tetrahydrafuran, and 412.9 mg (1.570 mmol) of triphenylphoshine were added. The reaction mixture turned yellow and was stirred for 10 min. at room temperature. 4.198 g (28.33 mmol) of (R)-methanesulfonic acid 1-methyl-prop-2-ynylester and 3.00 g (15.74 mmol) of 2-chloro-1-(2,4-difluorophenyl)-ethanone were added as well as 42.93 ml (47.22 mmol) of diethylzinc solution in toluene (1.1 M) within 5 min. at 25–35° C. dropwise; the mixture was intermittently cooled and subsequently stirred for 40 min. at room temperature. After pouring onto 50 ml of ice-cold water and 50 ml of aqueous 25% hydrochloric acid the mixture was extracted twice with each 50 ml of ethyl acetate. The organic phases were washed once with 50 ml of water, combined, dried over sodium sulfate and evaporated to dryness. 5.029 g of (2R,3S)-1-chloro-2-(2,4-difluoro-phenyl)-3-methyl-pent-4-yne-2-ol were obtained as a dark yellow oil (73% pure) containing 76% of the stated diastereomer, corresponding to a yield of 95.3%.

The NMR spectrum was identified to that described in Example 3.

EXAMPLE 5

18.29 g (259.5 mmol) of 1,2,4-triazole were dissolved in 120 ml of dimethylsulfoxide, and 7.061 g (173.0 mmol) of sodium hydroxide were added. The mixture was stirred for 20 min. at 70° C., cooled to room temperature, and a solution of 31.40 g (86.50 mmol) of (2R,3S)-1-chloro-2-(2,5-difluoro-phenyl)-3-methyl-pent-4-yne-2-ol (product of example 1) in 120 ml of dimethylsulfoxide was added. The mixture obtained was stirred for 3.5 hours at 70° C.

The reaction mixture was poured onto 1 l of ice-water and 80 ml of aqueous 25% hydrochloric acid, extracted twice with each 250 ml of toluene, the toluene phase extracted once with 50 ml of aqueous hydrochloric acid, the hydrochloric phases were combined, turned alkaline with about 150 ml of 6M potassium carbonate solution, extracted twice with each 250 ml of ethyl acetate, the organic phases washed twice with each 100 ml of water, combined, dried over sodium sulfate, the toluene phases extracted once with 100 ml and once with 40 ml of about 12% aqueous hydrochloric acid. The hydrochloric acid phases were combined, turned alkaline with aqueous 6M potassium carbonate solution, extracted twice with each 200 ml of ethyl acetate, the organic phases washed twice with each 150 ml of water, combined with the ethyl acetate phases from the first extraction, dried over sodium sulfate, concentrated to about 200 g, insoluble material was filtered off, the filtrate concentrated to about 130 g, 25 ml of 30% ethereal hydrochloric acid were added, and stirring was continued for 1 hour at room temperature and 1 hour at 0° C. The mixture was filtered and washed twice with each 30 ml of ethyl acetate at 0° C. to yield 19.5 g of (2R,3S)-1-[2-(2.5 difluoro-phenyl)-2-hydroxy-3-methyl-pent-4-ynyl]-1H-[1,2,4]triazol-4-ium-chloride (purity 80.6%) containing 87.4% of the stated diastereomer, corresponding to a yield of 57.9%.

NMR (DMSO): 0.93 (d,3H), 3.18–3.30 (m,2H), 4.6 (s,2H), 5.97 (s,1H), 6.9–7.2 (m, 3H), 7.6 (s,1H), 8.3 (s,1H).

EXAMPLE 6

15.12 g (214.5 mmol) of 1,2,4-triazole were dissolved in 120 ml of dimethylsulfoxide. 5.836 g (143.0 mmol) of sodium hydroxide were added, and stirring was continued for 20 min. at 70° C. The mixture was cooled to room temperature, and a solution of 24.81 g (71.49 mmol) of (2R,3S)-1-chloro-2-(2,5-difluoro-phenyl)-3-methyl-pent-4-yne-2-ol (from example 2) in 100 ml of dimethylsulfoxide was added. The mixture was stirred 3 hours at 70° C.

The reaction mixture was poured onto 1.5 l of water, extracted with 300 ml of toluene; separation was effected over glassfibre/filter paper. The aqueous phase was extracted with 300 ml of toluene and the organic phases twice with each 500 ml of water, subsequently with 200 ml of water and twice with each 50 ml of 2N aqueous hydrochloric acid. The aqueous phases were combined, made alkaline with 125 ml of 6M aqueous potassium carbonate solution, extracted three times with each 150 ml of ethyl acetate, the ethyl acetate phases washed twice with each 250 ml of water, combined, dried over sodium sulfate and filtered. After the addition of 5.309 g (57.19 mmol) of oxalic acid the mixture was concentrated to about 60 g, stirred 1 hour at 0° C., filtered and washed with 20 ml of ethyl acetate (0° C.) and with 20 ml ethyl acetate/n-hexane 1:1 gave 13.12 g of (2R,3S)-1-[2-(2,5-difluorophenyl)-2-hydroxy-3-methyl-penten-4-ynyl]-1H-[1,2,4]triazol-4-ium-oxalate (of purity 90%) containing 98.5% of the stated diastereomer was obtained, corresponding to a yield of 45.0%.

NMR (DMSO): identical with that of Example 5.

EXAMPLE 7

3.174 g (45.03 mmol) of 1,2,4-triazole were dissolved in 22.0 ml of dimethyl-sulfoxide. 1.225 g (30.02 mmol) of sodium hydroxide were added and the mixture stirred for 20 min. at 70° C. After cooling to room temperature a solution of 5.030 g (15.01 mmol) of (2R,3S)-1-chloro-2-(2,4-difluoro-phenyl)-3-methyl-pent-4-yne-2-ol (from example 4) in 20 ml of dimethylsulfoxide were added and the mixture was stirred for 3 hours at 70° C.

The reaction mixture was poured onto 100 ml of water, extracted twice with each 100 ml of toluene, the organic phases were washed with each 100 ml of water and then extracted once with 100 ml and twice with each 80 ml of aqueous 2N hydrochloric acid; the hydrochloric acid phases were combined, made alkaline with aqueous 6M potassium carbonate solution, extracted twice with each 80 ml of ethyl acetate, the ethyl acetate phases were washed twice with each 50 ml of water, combined, dried over sodium sulfate, filtered, washed with each about 20 ml of ethyl acetate and evaporated to dryness. 3.074 g of (2R,3S)-2-(2,4-difluoro-phenyl)-3-methyl-2-[1,2,4]triazol-1-yl-pent-4-yn-2-ol were obtained (purity 82%), corresponding to 46% yield. This was boiled 1 hour in 25 ml of t-butyl-methyl ether, cooled to 0° C., filtered and washed at 0° C. with t-butyl-methyl ether to yield 1.655 g of the product as white crystals which were 100% pure, corresponding to a yield of 39.8%.

NMR (CDCl$_3$): 1.0 (d,3H), 2.3 (s,1H), 3.2 (q,1H), 4.47 (s,1H), 4.85 (q×d,2H), 6.7–6.8 (m,2H), 7.2–7.5 (m,1H), 7.5 (s,1H), 7.9 (s,1H).

EXAMPLE 8

A solution of 27.51 g (128.6 mmol) of sodium (meta) periodate in 500 ml of deionized water was added to 71.30 mg (0.322 mmol) of ruthenium(IV)oxide hydrate within 5 min. at 0° C. The reaction mixture turned yellow. 101.3 μl (0.225 mmol) of ADOGEN® 464 were added, followed within 35 min. at 6–7° C. by a solution of 13.12 g (32.15 mmol) of (2R,3S)-1-[2-(2,5-difluorophenyl)-2-hydroxy-3-methyl-penten-4-ynyl]-1H-[1,2,4]triazol-4-ium-oxalate (from example 6) in 300 ml of acetic acid and 60 ml of deionized water, the last reactant added dropwise. After warming to room temperature the mixture was stirred for 2½ hours at room temperature.

80 ml of isopropanol were added to the reaction mixture, and stirring was continued for 10 min. at room temperature (pH 1.4), whereafter the pH was adjusted to 4 at 22–26° C. with about 280 ml of aqueous 4N sodium hydroxide solution, diluted with 600 ml of water, extracted six times with each 500 ml of ethyl acetate, the organic phases were combined, dried over sodium sulfate and evaporated. 18.9 g of brown semi-crystalline (2R,3R)-3-(2,5-difluorophenyl)-3-hydroxy-2-methyl-4-[1,2,4]triazol-1-yl-butyric acid were obtained, which were dissolved in 100 ml of ethyl acetate, boiled under reflux conditions for 30 min., the solution cooled with ice to room temperature, 15 ml of about is 30% ethereal hydrochloric acid were added, the mixture stirred for 1 hour at room temperature and 30 min. at 0° C., filtered, washed with ether and the obtained crystals dried for 2 hours under reduced pressure at 40° C. 12.75 g of the product were obtained as a white powder (purity 80%), containing 99.4% of the stated diasteriomer, corresponding to a yield of 95.1%. The compound has an m.p. of 162–178° C. (dec.).

NMR (DMSO): 0.88 (d,3H), 2.50 (s,1H), 3.12 (q,1H), 4.75 (d×d,2H), 6.0 (vb,1H), 6.9–7.0 (m,1H), 7.1–7.25 (m,2H), 7.71 (s,1H), 8.5 (s,1H).

EXAMPLE 9

2.499 g (11.68 mmol) of sodium (meta)periodate in 30 ml deionized water were added to 12.96 mg (0.0584 mmol) of ruthenium(IV)oxide hydrate within 10 min. at 0° C. The reaction mixture turned yellow. 8.264 mg (0.0205 mmol) of ADOGEN® 464 were added and subsequently a solution of 810.0 mg (2.921 mmol) of (2R,3S)-2-(2,4-difluoro-phenyl)-3-methyl-1-[1,2,4]triazol-1-yl-pent-4-yn-2-ol (from example 7) in 20 ml acetic acid and 2 ml of deionized water were added dropwise within 15 min. at 5–8° C. The mixture was stirred for 1 hour at room temperature.

2 ml of isopropanol were added to the reaction mixture, whereafter the pH was adjusted to 4 with about 40 ml of aqueous 2N sodium hydroxide, the mixture was diluted with 100 ml of water, extracted four times with each 40 ml of ethyl acetate, the organic phases combined, dried over sodium sulfate, filtered over 30 g of silicagel and evaporated to dryness. 893 mg of (2R,3R)-3-(2,4-difluoro-phenyl)-3-hydroxy-2-methyl-4-[1,2,4]-triazol-1-yl-butyric acid were obtained, which were heated under reflux condition in ethyl acetate for 20 min., cooled to room temperature and evaporated. 760 mg of the product were obtained containing 99% of the stated diastereomer, corresponding to a yield of 88%.

NMR (DMSO): 0.85 (d,3H), 3.1 (q,1H), 4.72 (d×d,2H), 5.8 (vb,1H), 6.8–6.90 (m,1H), 7.1–7.35 (m,2H), 7.6 (s,1H), 8.30 (s,1H).

EXAMPLE 10

In a glass pressure tube with magnet stirrer in an oil bath 250.0 mg (0.840 mmol) of (2R,3R)-3-(2,5-difluorophenyl)-3-hydroxy-2-methyl-4-[1,2,4]triazol-1-yl-butyric acid were dissolved in 10.00 ml of toluene.

219.0 μl (1.050 mmol) of hexamethyldisilazane and 534.8 μl (3.360 mmol) of O,O-diethyldithiophosphate were added and the mixture stirred for 16 hours at 125° C.

The reaction mixture was poured onto 12 ml of ice-cold aqueous 2N hydrochloric acid. The pressure tube was rinsed with 10 ml of toluene and 3 ml acetic acid. After the extraction the organic phases were reextracted with 5 ml of ice-cold aqueous 2N hydrochloric acid, the aqueous phases combined, made alkaline with 10 ml of aqueous 4N sodium hydroxide solution, extracted twice with each 25 ml of ethyl acetate, the organic phases washed with 10 ml of water, combined, dried over sodium sulfate and evaporated to dryness. 130 mg of (2R,3R)-3-(2,5-difluorophenyl)-3-hydroxy-2-methyl-4-[1,2,4]-triazol-1-yl-thiobutyramide were obtained as yellow foam which was dissolved in about 3 ml of methylene chloride:n-hexane 1:1, filtered, washed with 1 ml of methylene chloride:n-hexane 1:1 and the resulting crystals dried under reduced pressure at room temperature to yield 65 mg of the product as white crystals corresponding to a yield of 24.7%.

NMR (DMSO): 0.94 (d,3H), 3.60 (q,1H), 4.52 (d,1H), 4.85 (d,1H), 6.6 (s,1H), 6.9–7.25 (3m,3H), 7.60 (s,1H), 8.3 (s,1H), 9.95 and 10.1 (2s,2×1H).

This product can be converted in known manner to (2R,3R)-3-[4-(4-cyanophenyl)-thiazol-2-yl]-2-(2,5-difluorophenyl)-1-(1H-1,2,4-triazol-1-yl)-butan-2-ol, e.g. as in South African Patent 99/1763 (cf. Example 4h thereof).

EXAMPLE 11

10 g (27 mmol) of (2R,3R)-3-(2,5-difluorophenyl)-3-hydroxy-2-methyl-4-[1,2,4]-triazol-1-yl-butyric acid (oxalate salt) were dissolved in 200 ml of tetrahydrofuran and after addition of 5.8 g (35 mmol) 1,1'-carbonyldiimidazole stirred at 60° C. for 3 hours. After evaporation of the solvent the reaction mixture was poured onto 300 ml of aqueous 0.5N-HCl and extracted 3 times with each 300 ml of ethyl acetate. The extract was dried over Na$_2$SO$_4$ and evaporated. 7.1 g (94% yield) of (3R,4R)-4-(2,5-difluoro-phenyl)-3-methyl-4-[1,2,4]triazol-1-ylmethyl-oxetan-2-one resulted.

NMR (CDCl$_3$): 1.12 (d,3H), 3.98 (q,1H), 4.90 (d×d,2H), 7.05–7.20 (m,3H), 7.88 (s,1H), 8.14 (s,1H).

EXAMPLE 12

7.1 g (25.4 mmol) of (3R,4R)-4-(2,5-difluorophenyl)-3-methyl-4-[1,2,4]triazol-1-ylmethyl-oxetan-2-one were dissolved in 250 ml aqueous ammonia (NH$_4$OH 25%) and, after the addition of 64 mg (0.5 mmol) of dimethylaminopyridine, were stirred for 1 hour at room temperature. Evaporation of the reaction mixture gave crude 7.55 g (100% yield) of (2R,3R)-3-(2,5-difluoro-phenyl)-3-hydroxy-2-methyl-4-[1,2,4]triazol-1-yl-butyramide.

NMR (DMSO): 0.8 (d,3H), 3.20 (q,1H), 4.62 (d,1H), 4.74 (d,1H), 6.72 (s,1H), 6.89–6.95 (m,1H), 7.04–7.2 (m,2H), 7.6 (s,2H), 8.1 (s,1H), 8.3 (s,1H).

EXAMPLE 13

5.8 g (20 mmol) of (2R,3R)-3-(2,5-difluoro-phenyl)-3-hydroxy-2-methyl-4-[1,2,4]triazol-1-yl-butyramide were heated with 7.3 ml (78 mmol) of POCl₃ at 40° C. for 3 hours. After cooling to room temperature the excess POCl₃ was evaporated at reduced pressure to yield crude 10.3 g of (2R,3R)-3-(2,5-difluorophenyl)-3-hydroxy-2-methyl-4-[1,2,4]triazol-1-yl-butyronitrile which was used directly in the next step (Example 14).

EXAMPLE 14

6.16 g (20 mmol) of (2R,3R)-3-(2,5-difluorophenyl)-3-hydroxy-2-methyl-4-[1,2,4]-triazol-1-yl-butyrontrile were dissolved in 150 ml of tetrahydrofuran and, after the addition of 120 ml of a 20% aqueous solution of ammonium sulfide, the 2 phases of the reaction mixture were shaken at 60° C. for 4 hours. For work-up the reaction mixture was poured onto 250 ml of water and extracted twice with each 300 ml of ethyl acetate. The crude crystals were treated with 25 ml of t-butylmethylether at room temperature for 1 hour, filtered and dried. The first and second crop yielded 4.35 g (71%) of pure (2R,3R)-3-(2,5-difluorophenyl)-3-hydroxy-2-methyl-4-[1,2,4]triazol-1-yl-thiobutyramide.

The NMR spectrum was identical to that described in Example 10.

EXAMPLE 15

165 mg (0.55 mmol) of (2R,3R)-3-(2,4-difluorophenyl)-3-hydroxy-2-methyl-4-[1,2,4]triazol-1-yl-butyric acid were dissolved in 3.3 ml of tetrahydrofuran and, after the addition of 120 mg (0.72 mmol) of 1,1'-carbonyldiimidazole, stirred for 2 hours at 60° C. The reaction mixture was poured onto 10 ml of aqueous 0.5N HCl, extracted twice with each 25 ml of ethyl acetate, dried and evaporated to dryness. The crude residue was dissolved in 6 ml of aqueous 25% ammonium hydroxide and, after the addition of 2 mg of dimethylaminopyridine, stirred at room temperature for 1 hour. After evaporation of the reaction mixture the resulting residue was treated with 200 mg of POCl₃ at 40° C. for 3 hours. After evaporation of the excess POCl₃ under reduced pressure the crude product was poured onto water and extracted twice with 15 ml of ethyl acetate. The organic phase was dried with Na₂SO₄ and evaporated. Column chromatography on silica gel (eluent ethyl acetate/n-hexane=1:1) gave 95 mg (74%) of (2R,3R)-3-(2,4-difluorophenyl-3-hydroxy-2-methyl-4-[1,2,4]triazol-1-ylbutyronitrile.

NMR (DMSO): 1.05 (d,3H), 3.1 (q,1H), 4.70 (d×d,2H), 6.60 (s,1H), 6.95–7.05 (m,1H), 7.2–7.25 (m,1H), 7.30–7.40 (m,1H), 7.75 (s,1H), 8.40 (s,1H).

This compound can be converted to the thioamide in analogy to the above Example 14. The thioamide can then be converted in known manner to (2R,3R)-3-[4-(4-cyanophenyl)-thiazol-2-yl]-2-(2,4-difluorophenyl)-1-(1H-1,2,4-triazol-1-yl)-butan-2-ol, e.g. as in South African Patent 99/1763 (cf Example 4h thereof) or in EP 0 667 346 A2 (cf. Example 88 thereof).

The invention claimed is:

1. Halophenyl compounds of the formula

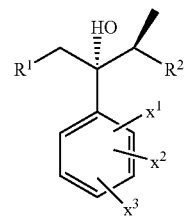

I wherein $R^1$ is halogen, lower alkylsulfonyl, phenylsulfonyl, p-tolylsulfonyl or 1H-1,2,4-triazol-1-yl and $R^2$ is ethynyl; $X^1$ is halogen and $X^2$ and $X^3$ are each independently hydrogen or halogen.

2. The process for the manufacture of halophenyl compounds of the formula

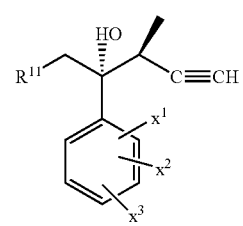

I-1 wherein $R^{11}$ is halogen, lower alkylsulfonyl, phenylsulfonyl or p-tolylsulfonyl, $X^1$ is halogen and $X^2$ and $X^3$ are each independently hydrogen or halogen, comprising reacting a halophenyl compound of the formula

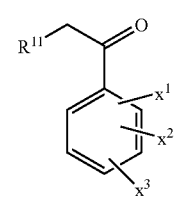

II wherein $R^{11}$, $X^1$, $X^2$ and $X^3$ are as above, with an alkyne of the general formula

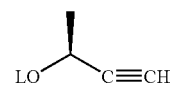

III wherein L is halogen lower alkylsulfonyl, phenylsulfonyl or p-tolylsulfonyl, in the presence of a palladium catalyst and an organometallic reagent in an apolar organic solvent.

3. The process according to claim 2, wherein $R^{11}$ is chloro.

4. The process according to claim 2, wherein L is lower alkylsulfonyl.

5. The process according to claim 4, wherein L is mesyl.

6. The process according to claim 2, wherein the palladium catalyst is a Pd(0)organic complex, a Pd(II)salt or an organic complex thereof.

7. The process according to claim 6, wherein the palladium catalyst is tetraphosphinyl palladium.

8. The process according to claim 6, wherein the palladium catalyst is palladium dichloride or its diacetonitrile complex.

9. The process according to claim 6, wherein the palladium catalyst is palladium diacetate or its diacetonitrile complex.

10. The process according to claim 2, which is carried out in the presence of a phosphine ligand.

11. The process according to claim 10, wherein the phosphine ligand is triphenylphosphine.

12. The process according to claim 2, wherein the organometallic reagent consists of an excess of a di-(lower alkyl)-metal reagent, in which the metal is selected from Li, Mg, Zn, Sn and Al.

13. The process according to claim 12, wherein the di-(lower alkyl)-metal reagent is a di-(lower alkyl)-zinc.

14. The process according to claim 13, wherein the di-(lower alkyl)-zinc is diethylzinc.

15. The process according to claim 2, wherein the apolar solvent used is selected from n-hexane, toluene and tetrahydrofuran.

16. The process of manufacturing a triazole carboxylic acid of the formula

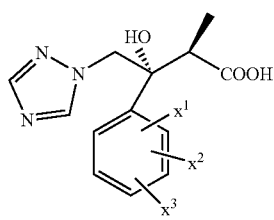

I-2 wherein $X^1$ is halogen, $X^2$ and $X^3$ are each independently hydrogen or halogen
comprising reacting a ketone of the formula

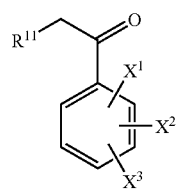

II wherein $R^{11}$ is halogen, lower alkylsulfonyl, phenylsufonyl, p-tolylsulfonyl; and $X^1$, $X^2$ and $X^3$ are as above, with an alkyne of the formula

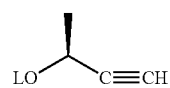

III wherein L is halogen, lower alkylsulfonyl, phenylsulfonyl, or p-tolylsulfonyl and $X^1$, $X^2$ and $X^3$ are as above in the presence of a paladium catalyst and an organometallic reagent in an apolar organic solvent to produce a phenyl hydroxy alkyne of the formula

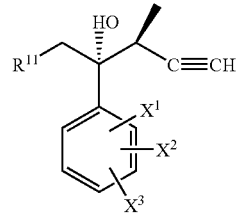

I-1 wherein $R^{11}$, $X^1$, $X^2$ and $X^3$ are as above
and thereafter reacting said phenyl hydroxy alkyne compound with 1,2,4-triazole to form said a hydroxy phenyl triazole of the formula I-3

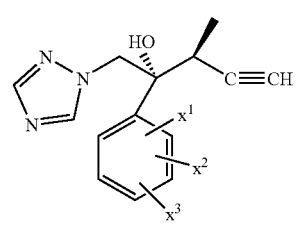

I-3 wherein $X^1$, $X^2$ and $X^3$ are as above;
and thereafter oxidizing said hydroxy phenyl triazole of the formula I-3 to form said triazole carboxylic acid of the formula I-2.

17. The process of producing a triazole carboxylic acid of the formula

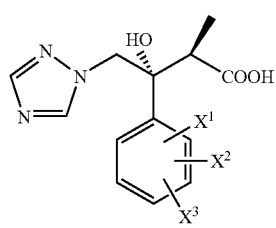

I-2 wherein $X^1$ is halogen and $X^2$ and $X^3$ are independently hydrogen or halogen; comprising reacting a halophenyl compound of the formula

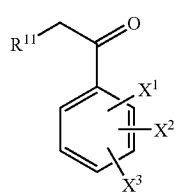

II wherein $R^{11}$ is halogen, lower alkylsulfonyl, phenylsufonyl, or p-tolylsulfonyl;
$X^1$, $X^2$ and $X^3$ are as above;

with an alkyne of the formula

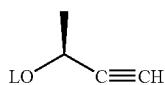   III wherein L is halogen, lower alkylsulfonyl, phenylsulfonyl, or p-tolylsulfonyl; in the presence of a paladium catalyst and an organometallic reagent in an apolar organic solvent to produce a phenyl hydroxy alkyne of the formula

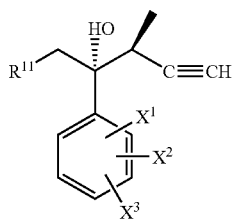   I-1 wherein $R^{11}$, $X^1$, $X^2$ and $X^3$ are as above;
oxidizing said alkyne halo phenyl carboxylic acid to produce an alkyne phenyl carboxylic acid of the formula

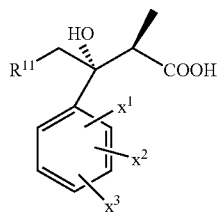   I-4 wherein $R^{11}$, $X^1$, $X^2$ and $X^3$ are as above; and thereafter reacting said alkyne phenyl carboxylic acid of the formula I-4 with 1,2,4-triazole to form said triazole carboxylic acid of the formula I-2.

18. The process according to claim 17, said alkyne phenyl carboxylic acid of the formula I4 is reacted with 1H-1,2,4-triazole in a polar or apolar organic solvent in the presence of a base.

19. The process according to claim 17, wherein the oxidation is carried out by means of an alkali metal periodate or hypochlorite in the presence of a catalyst.

20. The process according to claim 17, wherein the oxidation is carried out by means of sodium (meta) periodate in the presence of ruthenium dioxide.

21. The process according to claim 17, wherein the oxidation is carried out by means of an alkali metal permanganate.

22. The process according to claim 16, wherein the phenyl hydroxy alkyne of formula I-1 is reacted with 1H-1,2,4-triazole in a polar or apolar organic solvent in the presence of a base.

23. The process according to claim 22, where the base is an alkali metal hydroxide.

24. The process according to claim 22, where the base is an alkali metal hydride.

25. The process according to claim 22, wherein the solvent used is selected from dimethyl sulfoxide, dimethyl formamide, tetrahydrofuran and lower alkanols.

26. The process according to claim 16, wherein the oxidation is carried out by means of an alkali metal periodate or hypochlorite in the presence of a catalyst.

27. The process according to claim 16, wherein the oxidation is carried out by means of sodium (meta) periodate in the presence of ruthenium dioxide.

28. The process according to claim 16, wherein the oxidation is carried out by means of an alkali metal permanganate.

* * * * *